(12) United States Patent
Botto et al.

(10) Patent No.: US 11,971,373 B2
(45) Date of Patent: Apr. 30, 2024

(54) SYSTEMS AND METHODS FOR MONITORING SLOPE STABILITY

(71) Applicant: Muon Vision Inc., Cambridge, MA (US)

(72) Inventors: Tancredi Botto, Cambridge, MA (US); Ricardo Repenning, Santiago (CL); Francisco Arrau, Santiago (CL)

(73) Assignee: Muon Vision Inc., Cambridge, MA (US)

( * ) Notice: Subject to any disclaimer, the term of this patent is extended or adjusted under 35 U.S.C. 154(b) by 726 days.

(21) Appl. No.: 17/101,235

(22) Filed: Nov. 23, 2020

(65) Prior Publication Data
US 2021/0156810 A1 May 27, 2021

Related U.S. Application Data

(60) Provisional application No. 62/939,156, filed on Nov. 22, 2019.

(51) Int. Cl.
*G01N 23/2251* (2018.01)
*E21B 47/022* (2012.01)
(Continued)

(52) U.S. Cl.
CPC ....... *G01N 23/2251* (2013.01); *E21B 47/022* (2013.01); *G01N 9/24* (2013.01);
(Continued)

(58) Field of Classification Search
CPC ...... G01N 23/225; G01N 23/02; G01N 23/06; G01N 9/24; G01N 2223/505; G01N 2223/601; G01N 2223/606
See application file for complete search history.

(56) References Cited

U.S. PATENT DOCUMENTS

| | | |
|---|---|---|
| 8,384,017 B2 | 2/2013 | Botto |
| 2011/0001046 A1* | 1/2011 | Nagamine ............ G01N 23/22 |
| | | 250/306 |
| 2017/0268874 A1 | 9/2017 | Kasahara |

FOREIGN PATENT DOCUMENTS

| | | | | |
|---|---|---|---|---|
| AU | 2012203466 A1 * | 7/2012 | ............ | G01T 1/203 |
| CN | 208151458 U * | 11/2018 | | |

(Continued)

OTHER PUBLICATIONS

Anastasio et al., "The MU-RAY experiment. An application of SiPM technology to the understanding of volcanic phenomena", Nuclear Instruments and Methods in Physics Research, A 718 (2013) pp. 134-137.

(Continued)

*Primary Examiner* — David E Smith
(74) *Attorney, Agent, or Firm* — Rachel Greene; Troutman Pepper

(57) ABSTRACT

This disclosure relates to monitoring and assessing the mechanical stability and fluid accumulation in natural or man-made slopes comprising primarily of unconsolidated material, such as embankments, dams, roads, waste dumps, as well as man-made heaps of bulk materials that may occur in the stockpiling of grains, gravel, stones, sand, coal, cement, fly ash, salts, chemicals, clays, crushed limestone as well as heaps of mining ores, including crushed, milled and/or agglomerated ore, and run-of-mine materials.

15 Claims, 6 Drawing Sheets

(51) Int. Cl.
*G01N 9/24* (2006.01)
*G01N 23/02* (2006.01)
*G01N 23/06* (2018.01)

(52) U.S. Cl.
CPC ............ *G01N 23/02* (2013.01); *G01N 23/06* (2013.01); *G01N 2223/505* (2013.01); *G01N 2223/601* (2013.01); *G01N 2223/616* (2013.01)

(56) References Cited

FOREIGN PATENT DOCUMENTS

| | | | |
|---|---|---|---|
| JP | 2014126407 A | * | 7/2014 |
| JP | 2019152497 A | | 12/2019 |
| WO | 2013155075 A1 | | 10/2013 |
| WO | WO-2013155075 A1 | * 10/2013 | ............ G01N 23/06 |
| WO | 2019207046 A1 | | 10/2019 |

OTHER PUBLICATIONS

Bonechi et al., "Atmospheric muons as an imaging tool", Reviews in Physics, 5 (2020) 10038, pp. 1-28.
Bonomi et al., "Applications of cosmic-ray muons", Progress in Particle and Nuclear Physics, 112 (2020) 103768, pp. 1-48.
Menichelli et al., "A scintillating fibres tracker detector for archaeological applications", Nuclear Instruments and Methods in Physics Research, A 572 (2007) pp. 262-265.
"Slope stablilty analysis", Wikipedia, 2002 [retrieved from the internet on Jan. 15, 2021 (Jan. 15, 2021) at <https://en.wikipedia.org/wiki/Slope_stability_analysis>] para 1.

* cited by examiner

SYSTEMS AND METHODS FOR MONITORING SLOPE STABILITY

CROSS-REFERENCE TO RELATED APPLICATIONS

This application claims priority to U.S. Provisional Application Ser. No. 62/939,156 filed on Nov. 22, 2019, the content of which is hereby incorporated by reference in its entirety.

FIELD

This disclosure relates to monitoring and assessing the mechanical stability and fluid accumulation in natural or man-made slopes primarily including unconsolidated material, such as embankments, dams, roads, and waste dumps. This disclosure also relates to monitoring and assessing the mechanical stability and fluid accumulation in man-made heaps of bulk materials that may occur in the stockpiling of grains, gravel, stones, sand, coal, cement, fly ash, salts, chemicals, clays, and crushed limestone. This disclosure further relates to monitoring and assessing the mechanical stability and fluid accumulation in heaps of mining ores, including crushed, milled and/or agglomerated ore. This disclosure also relates to monitoring and assessing the mechanical stability and fluid accumulation in run-of-mine materials.

BACKGROUND

The monitoring of unconsolidated materials for mechanical stability and fluid accumulation is a significant challenge. Slope failures and landslides of unconsolidated materials, soft soils and sediments generally occur when the static stress due to the weight of the accumulation of material exceeds the shear strength of the material itself. The literature distinguishes between different failure modes such as translation failure, rotational failure, or wedge failure. Such monitoring is critical in the mining industry, where personnel are frequently in close proximity to large quantities of unconsolidated materials which pose an occupational hazard.

In some instances, mining ore is oxidized or calcined at high temperatures before being stockpiled in a heap for further processing. Unconsolidated materials may also be found in tunnels, including mining tunnels, and in general during the excavation of large pits, channels, roadways, and a variety of other earthworks. Stockpiles of unconsolidated materials are also found when transporting, storing, and shipping (for example, by boats such as bulk carriers) valuable materials such as ores, coal, and bauxite.

Also within the mining industry, large accumulations of unconsolidated materials are encountered in "heap leaching," which is a commonly used production technique for one or more base and precious metals including copper, gold, silver, nickel, and uranium. During heap leaching, large accumulations of unconsolidated are irrigated with a leaching solution. The unconsolidated materials frequently exceed 10 meters in height and can exceed 100 meters in height. The leaching solution is selected to cause the valuable minerals to leach from the ore.

The heap leaching process is a chemical extraction process that includes irrigating a large accumulation of unconsolidated material that includes mining ore that has been crushed or otherwise mechanically prepared with a chemical solution. Chemical extraction of metals by aqueous solution containing acids, salts and other agents is generally referred to as hydrometallurgy.

Heap leaching such metals frequently involves accumulations of unconsolidated materials which can exceed 10 meters or even 100 meters in height. A heap failure can severely damage valuable mining and material handling equipment and is hazardous to any person nearby. For leaching pads, that are generally built above a lined surface, the most common stability failure mechanism is due to block or translational type failure along the interface with the lowest shear strength parameters which is typically the liner. More complex compound failure modes are also possible.

Another problem is that in certain mining operations, sludges and fluids from a variety of chemical refining or hydrometallurgical processes accumulate in large tailing ponds. It is commonplace in the industry to build the retaining walls for such tailing ponds from excavated and potentially poorly consolidated material. The material contained in the tailing pond generally contains a large amount of water. Frequently, mine operators are interested in recovering the water contained in tailing ponds and recycle it back to the mining process. At the conclusion of mine operations, water contained in a tailing pond should be removed to enable soil reclamation and proper abandonment of the area according to environmental best practices. In many instances, tailing ponds and associated retaining walls remain after the conclusion of mining operations.

In most cases, slope failure occurs within an accumulation of unconsolidated material and depends strongly on the volume of fluids within the pore space of the material itself. The volume of fluids may change as a result of man-made irrigation, rain and snow accumulation, permafrost melt, or changing phreatic levels of the underlying water table. Excessive fluid accumulations lead to build up of pore pressure within the material, which in turn results in reduced frictional and cohesive strengths, for example, a loss of overall shear strength. Under these conditions, the slope of unconsolidated material will ultimately fail under its own weight. In the case of a mining heap, where fluid may be trapped in varying concentration due to complex fluid percolation patterns and flow barriers (such as permeability plugs), slope failure may also occur at the toe or at the top of the heap. In general, slope failure may also depend on the heterogeneity and size distribution of the unconsolidated material and the geomorphology of the terrain.

Sudden slope failure is also referred to as slope collapse or liquefaction and poses an ongoing risk for the mining, construction and cargo industries as well as whenever stockpiling of large quantities of materials occurs. It is also a natural risk, which may result for instance in landslide and soil movement across a variety of terrains and environments. These risks are often compounded by events such as heavy rains, snow melt and the occurrence of seismic events. Seismic events can trigger slope liquefaction by allowing sudden surge of excess pore water pressure or water build-up leading to a reduction in shear strength of the slope. Slope failure may lead to tragic loss of life, environmental damage, damage to specialized equipment or infrastructure, and significant loss of productive time.

In addition, for a given set of characteristics of the unconsolidated material (including its permeability, porosity, and/or coarseness) the optimal geometry and aspect ratio of a stockpile, retaining wall, or slope, including a man-made slope as a result of construction and engineering work, may be determined based on the actual volume of fluids present or expected to be present within the stockpile and on the availability of means of monitoring such volumes over large scales. An optimal stockpile or slope design may lead to preferred outcomes such as increased metal extraction from leaching heaps, longer asset lifetimes, continuity of operations, or increased safety of operations.

Dewatering is often used as a mitigation strategy against slope liquefaction or failure in, for example, open pit mining operations or to mitigate the settling or sinking of heavy structures such as buildings, bridges or foundations during construction or excavations. In mining, dewatering strategies are also used to allow the safe movement of heavy equipment and machinery, including surface equipment that must travel over areas that have been previously flooded, for instance by seasonal rains. However, dewatering can be a complex and expensive process with a wide range of techniques and equipment available. Improper deployment of dewatering strategies will not only result in excess costs, but it can also fail to prevent slope failure as intended.

Dewatering of active or previously abandoned mine tunnels and shafts is an ongoing concern for mine safety, particularly when these areas are difficult to access. Drilling or breaking through an abandoned mine tunnel filled with water can pose considerable risk of loss of equipment, asset value or even human lives. Many underground mines can only operate with pumps actively removing water that seeps from the subsurface into tunnels and other structures.

The risk of changing fluid levels is present in rocky but highly porous materials such as limestones or karst. Indeed, seasonal flooding can be a recurring problem in such areas and being able to monitor underground water tables can help in developing mitigating or dewatering strategies. A common associated phenomenon is the appearance of a sinkhole, which could occur in densely populated areas. For example, a sinkhole can occur when a rock surface gives way as it is being eroded from below by a rising water table.

Based on all of the above, there is continued need for monitoring and localizing (mapping) changing fluid levels deep within a large volume of earth, including a slope, a tunnel, or a shaft. Such monitoring is of interest not only to prevent slope failure, but also for planning and operating one or more of dewatering, water reclamation, soil reclamation, or spill mitigation. For example, knowledge of the amount of fluid present within the sludge and unconsolidated sediments contained in a tailing pond can inform the operator regarding the effectiveness and residual value left of any water reclamation and densification operations and the optimal location of pumps or drainage channels as well as how to plan the water reclamation and densification operations. In soil reclamation activities, densification is a primary objective where the desire is to return a wet soil to state with enough shear strength to sustain the weight of people, vehicles, buildings, reforestation, or the like without sinking or shifting. Densification requires eliminating most of the water that is trapped within the grains of the soil as a result of industrial processes such as mining operations. For these and other applications, having a way to directly monitor the density of soil is a critical need.

SUMMARY

This summary is provided to comply with 37 C.F.R. § 1.73, requiring a summary of the invention briefly indicating the nature and substance of the invention. It is submitted with the understanding that it will not be used to interpret or limit the scope or meaning of the claims.

In one embodiment, there is a method of monitoring slope stability by determining a density of at least a portion of a heap by measuring an incidence of atmospheric muons, the method comprising: associating one or more muon detectors with the heap by placing a muon detector within an overliner material, placing a muon detector within a trench, borehole, tunnel, or pipe that is located beneath an impermeable liner, placing a muon detector within a trench, borehole, tunnel, or pipe that is located within a first portion of the heap, placing a muon detector within a trench, borehole, tunnel, or pipe that is horizontally offset from the heap, placing a muon detector on a floor of a pit that is located between two or more heaps, placing a muon detector on a side surface of the heap, or a combination of the preceding placements, measuring an incidence of atmospheric muons on the one or more muon detectors, and determining the density of the at least a portion of the heap by comparing the incidence of atmospheric muons detected by the one or more muon detectors to a known muon attenuation of the materials in the heap and a known muon flux at the surface of the earth.

In another embodiment, comparing the incidence of atmospheric muons to a known attenuation of the materials in the heap includes one or more of: comparing the muon attenuation for a known density from an initial sample of the materials of the heap with the muon attenuation in the heap, comparing to the muon attenuation in the heap as measured during a prior time interval with the muon attenuation in the heap, comparing the muon attenuation of process fluids with the measured incidence of atmospheric muons on the one or more muon detectors, or comparing the muon attenuation in the heap to a known muon flux at the surface of the earth including a surface flux measured by a secondary detector.

In another embodiment, the initial sample of the materials of the heap is one or more of a dry ore sample, a pre-wetted ore sample, or agglomerated ore.

In another embodiment, the initial sample of materials of the heap is measured from two or more different locations in the heap.

In another embodiment, the measured incidence of atmospheric muons is measured by detecting at least two muon tracks that are oriented in different directions.

In another embodiment, there is also a step of moving at least one muon detector.

In another embodiment, associating one or more muon detectors with the heap includes placing a muon detector within an overliner material.

In another embodiment, associating one or more muon detectors with the heap includes placing a muon detector within a trench, borehole, tunnel, or pipe that is located beneath an impermeable liner or in between the first portion of the heap and a second portion of the heap.

In another embodiment, the heap includes two or more leaching pad area modules.

In another embodiment, associating one or more muon detectors with the heap includes placing a muon detector within a trench, borehole, tunnel, or pipe that is horizontally offset from the heap.

In another embodiment, the heap is a dam.

In another embodiment, associating one or more muon detectors includes placing at least one muon detector that is horizontally offset from the toe of the dam or placing at least one muon detector that is horizontally offset inside the dam and beneath the materials being held by the dam.

In another embodiment, associating one or more muon detectors with the heap includes placing a muon detector on a floor of a pit that is located between two or more heaps.

In another embodiment, associating one or more muon detectors with the heap includes placing a muon detector on a side surface of the heap.

In another embodiment, there further comprises determining a fluid content of at least a portion of the heap by measuring, for the portion of the heap that includes unconsolidated material, a change in the apparent bulk density of the unconsolidated material between an initial sample value and a current value.

In one embodiment, there is a system for monitoring slope stability by determining a density of at least a portion of a heap by measuring an incidence of atmospheric muons, the system comprising: one or more muon detectors associated with the heap by being located within an overliner material, within a trench, borehole, tunnel, or pipe that is located beneath an impermeable liner, within a trench, borehole, tunnel, or pipe that is located within a first portion of the heap, within a trench, borehole, tunnel, or pipe that is horizontally offset from the heap, on a floor of a pit that is located between two or more heaps, on a side surface of the heap, or a combination of the preceding locations, wherein the system measures an incidence of atmospheric muons on the one or more muon detectors, and wherein the system determines the density of the at least a portion of the heap by comparing the incidence of atmospheric muons detected by the one or more muon detectors to a known muon attenuation of the materials in the heap and a known muon flux at the surface of the earth.

In another embodiment, the heap includes two or more leaching pad area modules.

In another embodiment, the one or more muon detectors associated with the heap are located within a trench, borehole, tunnel, or pipe that is horizontally offset from the heap.

In another embodiment, the heap is a dam.

In another embodiment, the one or more muon detectors are associated with the dam by being placed horizontally offset from the heap outside of the dam or by being placed inside the dam and beneath the materials being held by the dam.

In another embodiment, one or more muon detectors are associated with the heap by being placed on a floor of a pit that is located between two or more heaps.

In another embodiment, one or more muon detectors are associated with the heap by being placed on a side surface of the heap.

In another embodiment, the system further determines a fluid content of at least a portion of the heap by measuring, for the portion of the heap that includes unconsolidated material, a change in the apparent bulk density of the unconsolidated material between an initial sample value and a current value.

Still further embodiments are also described.

In one embodiment, there is a method to determine volumetric fraction of fluids within an accumulation of non-consolidated material, such as a pile, a heap or tailing pond wall, underground mining tunnel, wherein the method is based on determining first a distribution of excess bulk density in the non-consolidated material from an analysis of the attenuation of the atmospheric muon flux traversing the accumulated material compared to the intrinsic matrix density of the non-consolidated material or its bulk density under initial conditions, including dry conditions or conditions at various compaction levels, wherein the muon flux traversing the accumulated material is measured along multiple directions from a muon detector having directional sensitivity and track reconstruction capabilities, and wherein the excess bulk density is further analyzed to determine the volumetric fraction of fluids or moisture content within the pore spaces of the non-consolidated material.

In another embodiment, the volumetric fraction of fluids is further analyzed in conjunction with a model of mechanical stresses within the non-consolidated material to determine a pore pressure within the accumulated material, and the volumetric fraction is determined using a model that accounts for soil compaction, and/or water evaporation to air and/or temperature changes in the heap.

In another embodiment, changes in the volumetric fraction of fluids are determined from an analysis of the distribution of excess bulk density measured over time.

In another embodiment, the accumulated pore pressure is utilized to determine the risk of liquefaction or collapse of the accumulated material, including the risk of slope collapse for the walls of an open pit or a retaining pond or a landslide risk.

In another embodiment, there is a method to determine the optimal processing time for mineral dissolution and metal extraction from a heap of crushed ore material based on a determination of the amount of process fluids, such as leaching fluids, across the heap.

In another embodiment, there is a method to optimize the economic value of said heap of crushed ore material based on an analysis of the amount of process fluids and its distribution across the heap, the processing time required for metal extraction from different areas across the heap and the risk of slope collapse or heap liquefaction due to accumulated pore pressure.

In another embodiment, there is a method wherein the optimization enabled by the determination of moisture content via a density measurement that utilizes atmospheric muons is performed leveraging a variety of external parameters such as the mineral composition of the material and its heterogeneity across the heap or the temperature profile across the heap.

In one embodiment, there is a method to reduce or optimize the consumption of leaching solution in a leaching pad for a given tonnage of recovered metal and an estimated net present value (NPV) of the asset.

In another embodiment, there is a method to determine the best remediation strategy and locate areas where intervention may take place to increasing extraction efficiency; such intervention may include altering the leachant flow in irrigation pipes or sprinklers in order to favor certain portions of the heap; other interventions may include creating drainage channels, including surface drainage channels or drainage boreholes, as well as intervention boreholes to deliver process fluids, air or bacteria control agents at depth.

In another embodiment, suitable remedial actions against slope collapse are determined from an analysis of the distribution of fluid volumes within the non-consolidated material.

In another embodiment, the suitable remedial actions include determining the optimal location and depth of dewatering holes drilled to reduce the accumulated pore pressure.

In one embodiment, there is a method to assess the stability of access roads and make an informed decision about the passage of heavy truck or machinery.

In one embodiment, there is a system for the determination of the flux and direction of atmospheric muons through the non-accumulated material wherein such system further comprises a segmented detector consisting of a combination of scintillation and Cerenkov detectors, wherein the scintillation and Cerenkov detector may have substantially different shapes or segmentation to further optimize the determination of the trajectory of the incoming atmospheric muons and the selection of signals exclusively due to ultra-relativistic particle radiation such as the atmospheric muon from other sources of nuclear radiation, including natural radioactivity due to materials and minerals contained in a heap of mining materials, and the light produced in either the scintillation or the Cerenkov detectors or both is collected by different optical fiber collimators, including collimators of different size, and independently routed to separate photosensitive channels or detectors via a multitude of optical fibers.

In another embodiment, the individual photodetector channels may belong to one of the groups of multi-anode photomultipliers, solid-state photodetectors (such as silicon photomultipliers), electron multipliers, micro-channel plates and scientific cameras, including any combination thereof.

In another embodiment, the photosensitive detectors are separable from the combination of scintillation and Cerenkov detectors and the position of the photosensitive detectors position within the system for measuring the atmospheric muon flux is optimized in terms of space and geometrical constraints.

In another embodiment, the segmented optical detector elements are placed across multiple parallel planes separated by a distance optimized for the purpose of optimizing an angular resolution with which the incoming atmospheric muon directions are determined.

In another embodiment, the segmented optical detector elements are placed in the outer annulus of a cylindrical tool suitable for placement in a borehole.

In another embodiment, at least one muon detector is placed on a conveyance and the conveyance includes one or more of a pulley, a rail system, or traction generating wheels that allow the muon detector to move to different points under the heap of material that is being monitored, and the borehole has an opening at each distal end to thereby provide measurements at different view angles or to allow for maintenance and re-utilization of the detector.

In one embodiment, there is a system of distributed muon detector including an array of non-powered optical sensing units consisting of a combination of segmented scintillator and/or Cerenkov detectors, wherein the multiple optical signals from the different and substantially well separated optical sensing units are collected via optical fibers and routed with minimal signal loss to an independent signal processing unit.

In another embodiment, there is at least one independent processing unit further comprising a power supply, a combination of multi-channel photodetectors or multiple photodetectors, and multi-channel digitizing electronics.

In another embodiment, the independent processing unit further comprises data ports for data transfer and control, or a dedicated networked computer including as a computer with a wireless or a wired data connection.

In another embodiment, the distributed sensing units and the light-collecting optical fibers are buried in a trench, such as trench under a heap of mining material or in the overliner section of leaching heap, or placed across multiple hole located around an accumulation of non-consolidated material.

In another embodiment, there is a semi-autonomous system for the detection of atmospheric muons that is battery operated and optionally includes one or more of a solar panel array, a wind turbine, a gasoline generator, a natural gas generator, or a diesel generator.

In one embodiment, there is a method to facilitate the remediation of wet soils, such as from tailing ponds, based on a measurement of the density of the moisture rich material based on which the shear strength of the remediated material can be determined.

In one embodiment, there is a method to facilitate the water recovery from tailing ponds based on the measurement of the overall density due to the accumulation of coarse grains, fines and sediments, with which to determine the amount of free water recoverable.

In one embodiment, there is a visualization interface to displace moisture content or measured density from a system of muon detector wherein the data is shown in 2D projection overlaying the presence of irrigation lines and mining equipment in a spatially realistic manner.

In another embodiment, the visualization interface is configured to display of trends of moisture content over time for each of the measurement voxels, including displaying over-saturation or under-saturation conditions that relate to the risk of slope collapse or poor efficiency for metal extraction by leaching.

In one embodiment, there is a method for determining the location and distance from pre-existent tunnels when performing underground mining drilling operations, for instance in order to reduce risk of intersecting of preexisting tunnels that may be filled with water.

In one embodiment, the system is portable and configured to be transported around an underground mine by a vehicle to survey with only one sensor.

DRAWINGS

Aspects, features, benefits and advantages of the embodiments described herein will be apparent with regard to the following description, appended claims, and accompanying drawings where:

DETAILED DESCRIPTION

Figure 1:
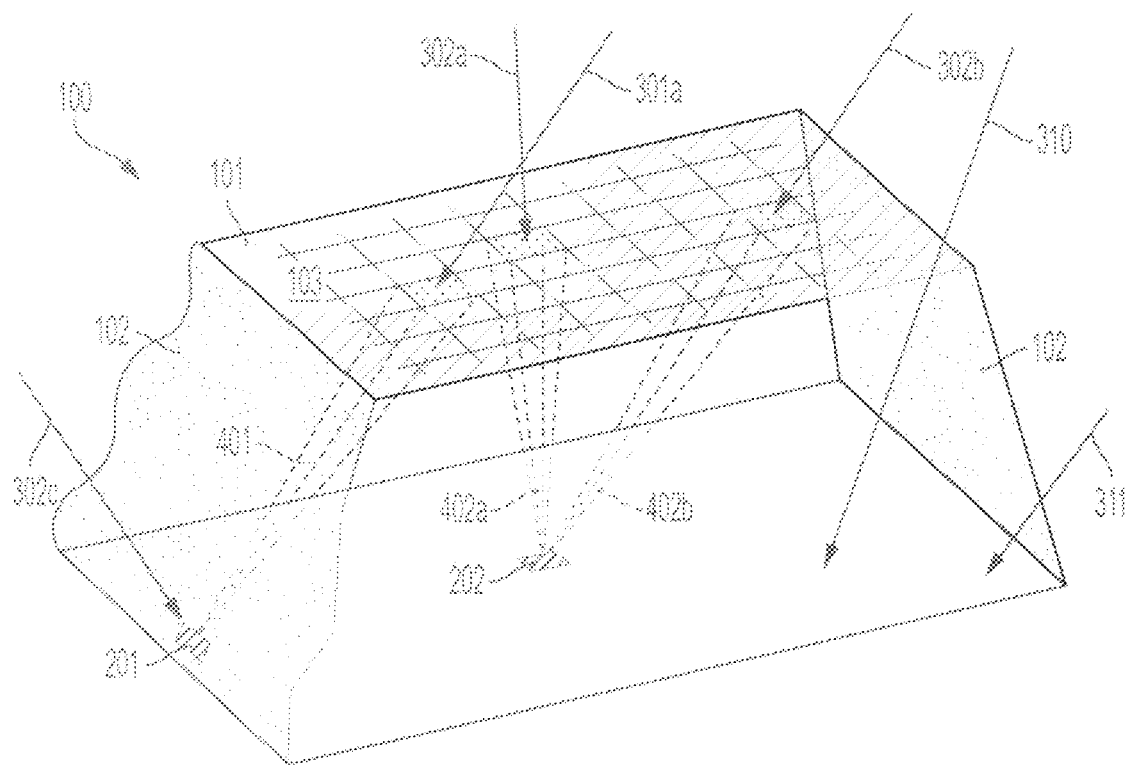
FIG. 1 is a schematic view of at least a portion of a system in accordance with the present disclosure.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The present disclosure offers an alternative method with which to monitor slope stability as well as determine fluid volumes within a large structure such as a stockpile, a mining leaching heap, a pond retaining wall, a man-made dam, an underground tunnel, an open pit, or an access road. The systems and methods described herein are based on a direct measurement of the excess bulk density due to the accumulation of fluids which can be directly interpreted in terms of total fluid mass or volume within the unconsolidated material. The disclosure is not limited and is applicable to monitoring the stability of the walls of open pit and underground mines as well as the stability of bulk cargo or stockpiled materials.

As used herein, the terms "heap," "stockpile," "wall," or "walls" mean a mass of unconsolidated material. As described above, the specific form of the unconsolidated material that makes up the heap, stockpile, wall, or walls is not limited and includes one or more of stockpiles, pond retaining walls, pond retaining dams, man-made dams, underground tunnel, open pit, or access road.

As used herein, "unconsolidated material" means sediment that is loosely arranged or unstratified, or whose particles are not cemented together, found either at the surface or at depth.

A measurement of bulk density is determined by way of measurement of the event rate of atmospheric muons passing through the volume of unconsolidated material under investigation. Atmospheric muons are part of the natural cosmic ray flux and arrive from space everywhere on the surface of the earth. The flux of the atmospheric muons is measured by the number of particles passing within a solid, angle-centered around a given direction, per unit of time. Similar to X-ray radiography and for a given incoming muon flux, the attenuation of the muon flux through a given section of a heap, dam wall, walls of an open pit, underground, or the like, is dependent on the average bulk material density integrated along the particle (muon) trajectory through the volume under investigation. The bulk density so measured is the average density due to all materials within the volume under investigation, including rock grains, fluids and empty pore spaces. By measuring the muon flux though such an object of interest along different directions, it is possible to form a map of the bulk density distribution.

Measurement of muon flux is obtained with one or more muon detectors which can be positioned at different view angles with respect to the object or volume under investigation. From the measurements of muon flux through the volume, a three dimensional tomographic density map can be formed. In some embodiments, a single measurement point is provided, and the density information remains three dimensional in nature but can be represented by a two dimensional projection. In other embodiments, multiple measurement points are provided.

As described herein, each muon detector is able to detect the passage of single-particle muon events and is also able to determine the direction of the single-particle muon events. The muon detectors are not limited and include one or more of scintillator detectors, gas detectors, solid state detectors (e.g. silicon detectors and TFT arrays), transition radiation detectors, and Cerenkov detectors.

As will be understood by those of skill in the art, the density of the initial phase of the unconsolidated material is measured separately in situ or is a known value. The initial phase of the unconsolidated material includes one or more of a dry ore material, a pre-wetted ore material, or an agglomerated ore material. In certain embodiments, the density of the initial phase of unconsolidated material is measured by obtaining multiple samples from different locations in the mining operation.

After the density of the initial phase has been measured separately or the density is otherwise ascertained, it can be used in computations to determine fluid content. Any change in the apparent bulk density of the unconsolidated material versus the initial phase, to include spatial changes or changes over time due to an approaching fluid front, can be interpreted as the change due to the presence of fluid volumes in the unconsolidated material. The average bulk density $\rho_b$ of the unconsolidated material governs the muon flux, and $\rho_b$ is given by Equation 1, where $\phi$ is the porosity of the matrix of the unconsolidated material and $\rho_m$ is the density of the matrix. In Equation 1, no fluid is present and the contribution of air is neglected.

$$\rho_b=(1-\phi)\rho_m \tag{1}$$

For materials with a pore space fully or partially filled by fluids, the bulk density is shown by Equation 2, where S is the fraction of empty pore space in the material occupied by the fluid, also known as fluid saturation in the material, or moisture of the material, and $\rho_f$ is the density of the fluid.

$$\rho=\rho_b=(1-\phi)\rho_m+\phi S\rho_f \tag{2}$$

For the cases mentioned above, including that of a leaching fluid percolating through a heap, $\rho_f$ is well known and approximately equal to the density of water. Thus, a measurement of a representative, well-mixed sample of dry or initial materials provides a direct measurement of its porosity, whereas a comparison between the apparent density under dry or initial condition and saturated condition yields a direct determination of the fluid saturation S. In many cases, $\phi$ is known or can be determined beforehand and therefore any measurement of an excess bulk density distribution in a heap or a wall is a direct measurement of the fluid that is contained in the heap or wall. Adjustments can also be made, as is appreciated by those of skill, to account for the heap compacting or settling by way of its own weight. When this measurement is performed from a single muon detector with the required particle tracking capabilities an accurate 3D analysis of the distribution of fluids is obtained. When multiple detectors are used, further constraints can be placed on the density distribution or the coverage can be extended.

Because muons are highly penetrating, energetic subatomic particles, the investigated volume can be very large. In certain embodiments, heaps can be tens of meters high. In other embodiments, thick walls can be investigated, including retaining walls for tailing ponds that are frequently used in mining operations. The volume of unconsolidated material that can be investigated can be at least about 10 m$^3$, at least about 100 m$^3$, at least about 1000 m$^3$, at least about 100,000 m$^3$, at least about 500,000 m$^3$, or at least about 1,000,000 m$^3$, and closed ranges that are formed by combining two or more of the preceding values as endpoints.

The average flux of atmospheric muons on Earth is well known to have different intensities at different elevations and latitudes. In addition, it may slowly change over time due to effects related to the solar activity cycle and any induced variations in the Earth's magnetosphere in space. Other variations may come from changes in the overall density throughout the atmospheric air column such as seasonal changes. Finally, the muon flux at very high angles from the vertical could be affected by the presence of geographical features such as the presence of nearby mountains that could effectively act as a filter. These variations can introduce a systematic error in our measurement of the muon opacity, which is the effective muon flux attenuation through bulk matter.

It is possible to minimize systematic effects due to uncertainties in muon flux normalization by either utilizing one or more reference detectors by normalizing at least one density map to the muon flux measured along a fixed reference direction, or by normalizing at least one density map to a map taken during a previous time interval. In the case of normalizing density maps to the muon flux measured along a fixed reference direction, it is possible to reconstruct a relative density map in the spatial sense that is still of value in assessing slope stability. In certain preferred configurations, it is also possible to normalize to the overall atmospheric muon flux by utilizing muon tracks that arrive at the detector from a direction outside the region of interest or the volume under investigation. This is referred to as sideways track normalization. For example, in heap or wall monitoring, a detector placed on the outer surface of the heap will be able to distinguish muon tracks that have traversed the heap (and thus carry information about its density) from tracks arriving at the opposite side of the detector that carry information about the local atmospheric muon flux which is required for the normalization of the muon opacity measurement. The disclosure contemplates similar configurations for monitoring open pit walls, cargo, and other accumulation of bulk materials.

FIG. 1 illustrates an exemplary embodiment of the disclosure. In FIG. 1, muon detectors 201 and 202 are placed around a section of a heap of material 100, which can be a heap of mining ore in a leaching pad. Heap 100 further comprises two side walls 102 and a top surface 101. It should be noted that although heap 100 is depicted in FIG. 1 as having a flat, rectangular top surface, the shape of the heap is not so limited. Heaps can have irregular shapes, including shapes with different elevations or a non-polygonal contour. Muon detector 201 is placed sideways on the heap and muon detector 202 is placed beneath the heap. A plurality of muon particles originating from space traverses the heap first by passing through the top of the heap and subsequently arriving at muon detectors 201 and 202. The muon particles traverse the heap in all possible directions. Muon detectors 201 and 202 can detect the arrival of each muon particle on their surface and determine the muon incoming direction event by event. According to FIG. 1, muon tracks 301a and 302b traverse the heap 100 and arrive at detector 201, and muon tracks 302a and 302b traverse the heap 100 and arrive at detectors 201 and 202. Muon track 302c does not traverse the heap but nonetheless arrives at detector 201. Muon tracks 310 and 311 also traverse at least a portion of the heap 100 but because such tracks do not arrive at any muon detector, their arrival and direction is not registered. Those skilled in the art recognize that in some embodiments, muon detectors 201 and 202 intrinsically have angular resolution such that muon arrival tracks can only be determined within a certain solid angle and that this angular resolution is different for muon particles that arrive from different directions. Furthermore, density and fluid information may be obtained after sufficiently high event statistics are accumulated over time. Thus, in certain embodiments, muon tracks are grouped over 3-dimensional voxels that are larger than the solid angle due to the muon detectors' resolution. Muon tracks that belong to a particular voxel are summed and analyzed together to calculate the average value of the bulk density and/or the amount of fluid within the volume of the voxel itself.

For example and referring again to FIG. 1, the surface 101 of the heap 100 is subdivided into a grid 103, with each pixel on the grid defining the base of truncated pyramid voxels 401, 402a, and 402b, each traversed by a small subset of the overall muon flux. Because of the directional nature of the muon detectors' resolution and combined with the orientation of the muon detector, the muon flux can be mapped in a three dimensional manner.

The size and shape of each pixel in the grid 103 is not limited and can be modified when the density map is displayed. In some instances, it may be advantageous to choose a finer or coarser grid as a function of the available statistic. For instance, the grid spacing can be chosen on the basis of the uncertainty with which the bulk density can be determined due to the intrinsic statistical nature of the measurement, including choosing a grid with a non-uniform spacing or a grid defining inverted pyramidal voxels with an increasing base area (on top of the heap) as one moves further away from the location of the muon detector located under the heap. In particular, as the muon rate decreases for larger muon angles relative to the vertical, the statistical accuracy of the method decreases and can be improved by increasing the pixel size, for example, trading position reconstruction in favor of measurement accuracy. In certain other cases, the grid 103 may become denser, and the volume of each voxel 401, 402a, and 402b may shrink over time as more and more muon tracks are measured at the detector. In such cases, one may effectively choose to trade off an increased measurement sensitivity for an increased position resolution over time as defined by choice of pixel areas across the volume. In still further embodiments, the pixels can have a non-rectangular base, for example the base of the pixel can be an arc segment. In such an embodiment, instead of a square grid, the pixel would be arranged to form concentric circles or arc segments.

Those skilled in the art will understand that the muon track data in a muon detector can be simultaneously collected across many directions and can be organized in an arbitrary number of voxels. When multiple detectors are deployed in a heap, some of the voxels may intersect each other, which may further constrain the three dimensional analysis of the density across the heap.

Those skilled in the art will also understand that in embodiments where a muon detector is positioned near the edge of a heap, the muon detector will also measure sideways muon tracks such as track 302b that will provide an independent, local measurement of the incoming atmospheric muon flux, or of a muon flux unaffected by the water content within the volume under investigation. When such independent measurements are obtained, they can normalize the apparent muon flux that is measured by other muon detectors.

The number, position, orientation, and size of the muon detectors is not limited. The muon detectors can be selected, oriented, and positioned based on survey design optimization techniques that account for the shape of the volume of unconsolidated material under investigation, the thickness of the unconsolidated material, the desired accuracy on the density measurement for a particular observation time, the overall cost for muon detector hardware, and the ease of installation and thus cost of installing the muon detectors. In most instances, the survey design optimization is performed based on forward model simulations that predict an expected count rate as a function of at least one of the position of the muon detectors, the segmentation of the muon detectors, and track reconstruction efficiency and accuracy. Such survey design optimization can also be used to determine the shape, size, and orientation of each muon detector as well as the orientation of the active detector elements that determine the muon tracks.

In certain embodiments, one or more of the muon detectors are segmented. The segmentation is not limited and includes layering detector planes or surfaces containing individual sensing elements in a crossing pattern (such as simple X-Y patterns, chevrons, helicoidal patterns). Segmentation provides the capability to measure multiple points along the muon direction, which allows a rectilinear track to be reconstructed. In such embodiments, the segmentation determines the track-resolving capabilities of the detector. Segmentation ultimately determines the track-resolving capabilities of the detector. Greater segmentation will typically yield a more accurate track reconstruction, which could be used to obtain a finer reconstructed density map. However, segmentation also increases the muon detector cost because it increases the number of required sensing elements and the number of required electronics channels.

The construction of the muon detectors is not limited, and includes one or more Gas Electron Multipliers (GEM), wire chambers, liquid chambers, and/or time projection chambers which are able to reconstruct a muon track by utilizing the information left by the muon ionization track in a single gas volume.

In many heap density mapping applications, it may be advantageous to place the muon detector at the base of the heap and bury the muon detector underneath the heap as the heap is being built. Alternatively, the muon detector can be placed within or on the overliner material or under the leaching pad by burying it, or the muon detector can be placed directly on the fluid impenetrable liner of the leaching pad. In some embodiments, the muon detector can be placed under the fluid impenetrable liner. The placement of the one or more muon detectors can be achieved by way of at least one of a hole, a trench, a horizontal borehole, a vertical borehole, a slanted borehole (i.e. drilled at an angle) or a directional drilling borehole (this is different than slanted, i.e. a well that changes direction). Placing the muon detector in these ways maximizes the view angle of the muon detector or of a system that includes a plurality of muon detectors.

In heap leaching, the operator needs to recover the pregnant leaching fluid that traversed the material because the pregnant leaching fluid has elevated amounts of dissolved metals and contains the extracted metal. For this purpose, leaching pads are built on top of a fluid impenetrable liner. Immediately above the liner is a layer that is referred to as the overliner section. The overliner section includes a matrix of overliner material that is highly permeable to facilitate the collection of pregnant leaching fluid and the dissolved metals that are contained therein into collection pipes for transportation to a treatment plant (typically, a solvent-extraction and electro-winning plant). The ore material to be processed is placed or stacked on the overliner. After processing is complete, the ore material can be removed and discarded in order to provide a place for newly extracted ore to be placed on the leaching pad. Re-use of an existing leaching pad can be economical and minimizes the area required for mineral processing. A plurality of collection pipes are placed within the overliner material to collect the pregnant leaching fluid.

In certain other embodiments which are referred to herein as static heap leaching, a multi-step process is employed. During static heap leaching, a first liner is positioned in a location, and a first ore volume is deposited on the first liner. The first liner is fluid impermeable and collects any fluid that seeps through any ore volume that is positioned above the first ore volume. The first ore volume is irrigated and a first pregnant leaching fluid is collected in order to extract metals. After the irrigation and collection of a first pregnant leaching fluid are completed, a second liner is optionally placed on the first ore volume, and a second ore volume is deposited on the optional second liner. While two layers of liner and ore volume are described above, any number of alternating liners and ore volumes can be provided, and additional liners are not necessarily required above the first liner. Between each ore pair of ore volumes, the liners are optional. However, as described above, there must be at least one liner present below the lowest ore volume in order to collect any fluid that seeps through any ore volume that is positioned above the line. In static heap leaching, when the irrigation of an ore volume is stopped and a new liner is placed on the ore volume, the density of the ore volume does not change substantially. Thus, for ease of analysis, any density changes of the heap over time can be attributed to additional ore which is quell deposited.

Figure 2:
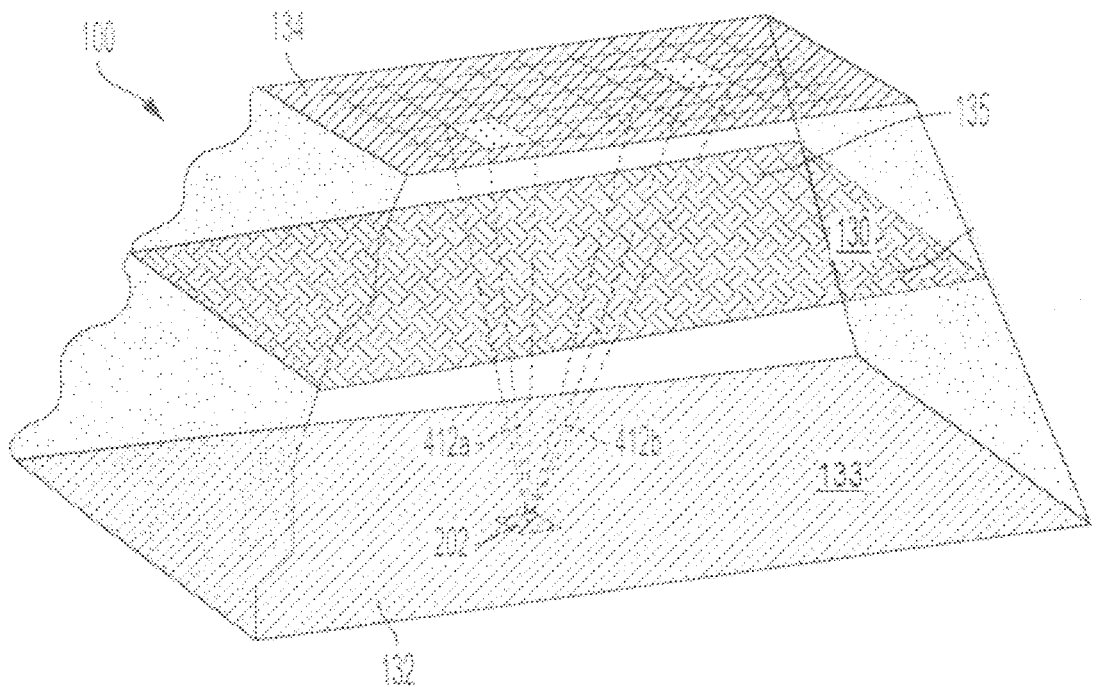
FIG. 2 is a schematic view of at least a portion of a system in accordance with the present disclosure.

FIG. 2 depicts an embodiment of static heap leaching. In FIG. 2, heap 100 includes a first liner 133, a first ore volume 132, an optional second liner 130, and a second ore volume 135. As described above, the second liner is impermeable to fluids that are irrigated from the top of the heap 100, thereby preventing fluids from entering the first ore volume 132. When muon detector 202 is placed at the bottom of the first ore volume 132, the top surface 134 is divided into pixels defining density voxels 412a and 412b. In FIG. 2, any density change that is observed in the voxels can be attributed to fluid entry or fluid exit in the second ore volume 135.

Static heap leaching can include 1 ore volume, 2 ore volumes, 3 ore volumes, 4 ore volumes, 5 ore volumes, 6 ore volumes, 7 ore volumes, or 8 ore volumes. As previously described, each layer can optionally include a liner. If a liner is included, an overliner layer can optionally be included on top of and contacting the corresponding liner. Where no additional liners beyond the first liner are included, fluid seeps from the topmost ore volume, through any intervening ore volumes, and finally to the overliner layer and corresponding liner which serves to collect the now pregnant leaching fluid which is laden with dissolved metals.

FIG. 2 depicts an embodiment of static heap leaching. In FIG. 2, heap 100 includes a first liner 133, a first ore volume 132, an optional second liner 130, and a second ore volume 135. As described above, the second liner is impermeable to fluids that are irrigated from the top of the heap 100, thereby preventing fluids from entering the first ore volume 132. When muon detector 202 is placed at the bottom of the first ore volume, the top surface 134 is divided into pixels defining density voxels 412a and 412b. In FIG. 2, any density change that is observed in the voxels can be attributed to fluid entry or fluid exit in the second ore volume 133.

In another embodiment, metals are extracted from the ore by dynamic heap leaching. In dynamic heap leaching, so-called on stacks and off stacks are built and dismantled in succession at the end of the treatment process. In this case, a muon detector placed at the bottom of the heap can be re-utilized over time to analyze multiple stacks. In dynamic heap leaching, it is convenient to place the detector either below the base liner of the pad or within the over-liner material.

In other cases, the heap leaching process is adapted to the morphology of the terrain. For instance in valley fills or valley leaching operations, leaching pads are placed at the bottom of a valley, with the natural slope providing a convenient way to collect process fluids percolating through the stack of crushed ore. In these cases, because at least some portions of the surrounding terrain are above the stack of crushed ore, muon detectors may be placed in boreholes, tunnels or caves excavated on the side of the valley fill.

Generally, it is important that any surveying muon detectors do not interfere with the operation of equipment such as bucket wheel excavators and moving ore conveyors used to build or disassemble the heap. In some embodiments, it may be convenient to place the detector in a borehole, including a slanted borehole, drilled so as to be able to position the detector directly under the heap even though at a certain depth under the base liner. Multiple boreholes could be used, including horizontal boreholes or tunnels excavated at greater depths under the heap. To improve coverage, multiple muon detectors may be placed at different positions along the same borehole or within multiple boreholes.

In some embodiments, the muon detector is positioned within a pipe and is configured to be movable within that pipe, and the pipe is located at the base of the heap. When the muon detector is positioned within a borehole, tunnel or pipe, it becomes possible to move the muon detector to different positions under the heap to more cost-effectively cover larger volumes. In these configurations, the position of the detector can be changed according to either the construction schedule of the heap or the associated mineral processing operations. Such configurations are referred to as movable muon detectors.

The movement of the movable muon detectors is not limited. The propulsion source of the movable muon detectors can be an internal propulsion source or an external propulsion source. Internal propulsion sources include one or more of an integral electric motor, an integral internal combustion engine, a propeller, a turbine, a jet, or a thruster. External propulsion sources may include elevated liquid or gas pressure within the borehole, tunnel, or pipe in a similar manner to pigs that are used within petroleum pipelines, and cables that are used to pull the muon detector. When a cable is used to move a muon detector, it is referred to as a tethered muon detector. The cable that is used in conjunction with the muon detector can provide one or more of electrical power, data connections, or liquids or gases under pressure (such as compressed air). The cable can be armored to prevent damage. It is also contemplated that a single cable or plurality of cable segments together can move multiple movable muon detectors at the same time along a borehole, tunnel, or pipe. This allows for re-use of the same sensor according to the operation schedule in, for example, a dynamic leaching heap. Movable muon detectors can also be spaced according to the need of the measurement, for example to provide multiple view angles or different spacing options, all without interfering with operations at the surface of the heap. The movable muon detectors can be moved by way of a powered winch system or even a hand crank system. A movable muon detector offers additional advantages in that it can be retrieved to permit maintenance operations or replacements. Finally, different combinations of multiple surface, borehole and side detectors are contemplated in order to assemble an optimal survey of the heap under consideration.

Figure 3:
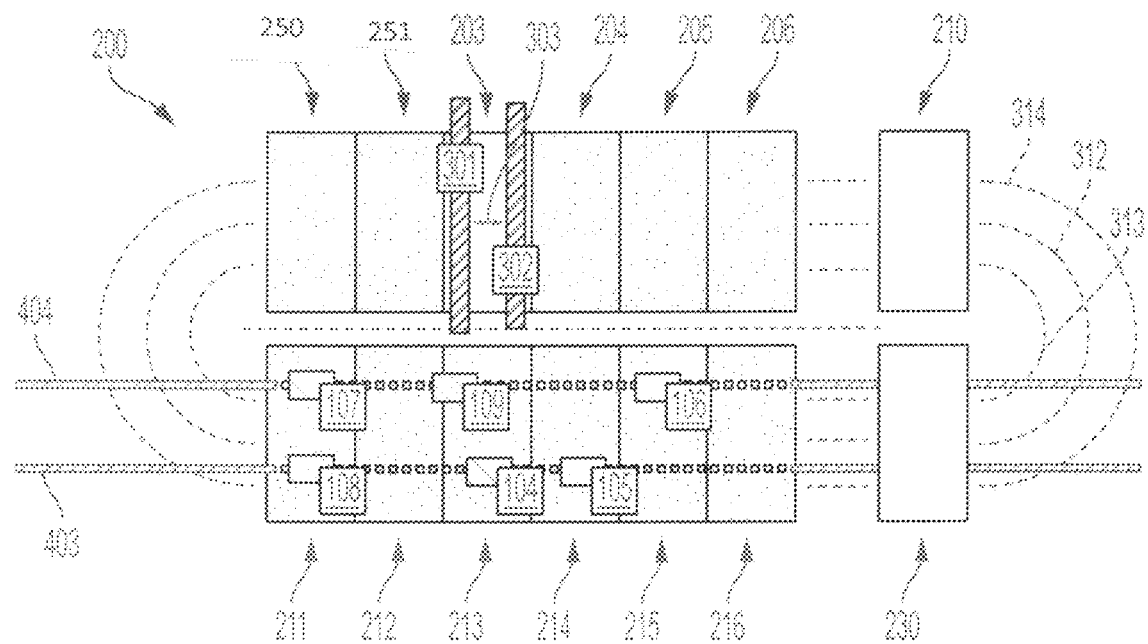
FIG. 3 is a schematic view of at least a portion of a system in accordance with the present disclosure.
Figure 4:
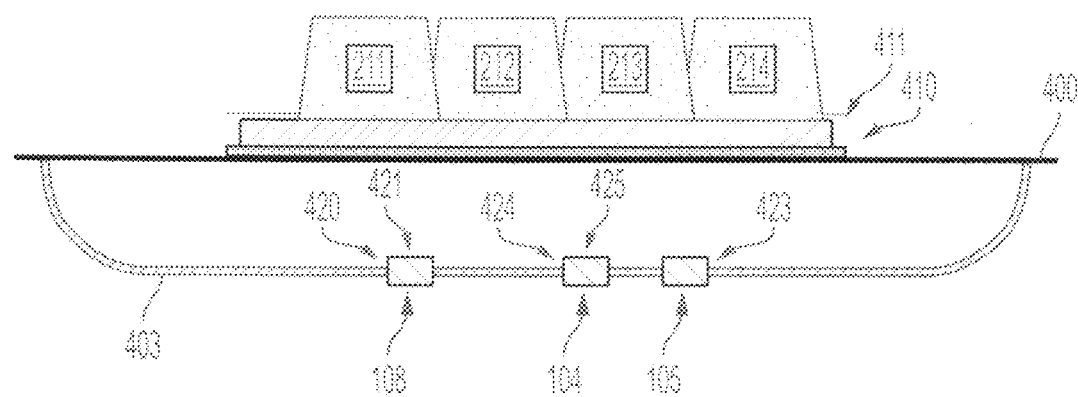
FIG. 4 is a schematic view of at least a portion of a system in accordance with the present disclosure.

FIG. 3 and FIG. 4 each depict an embodiment of the disclosure. FIG. 3 depicts a top view of a dynamic leaching pad, and FIG. 4 depicts a side view of the leaching pad of FIG. 3. The leaching pad area 200 includes one or more leaching pad area modules 250, 251, 203, 204, 205, 206, 210, 211, 212, 213, 214, 215, 216, and 230. The size of the leaching pad area modules is not limited and depends on the associated mining operation. In some embodiments, the leaching pad area modules have a width of about 50 m, and a length of about 150 m. Leaching pad area modules 250, 251, 203, 204, 205, 206, 210, 211, 212, 213, 214, 215, 216, and 230 are continuously emptied and filled by moving equipment such as a movable bucket wheel excavator 301 and a movable stacker 302. The movable bucket wheel excavator 301 and the movable stacker 302 may move on rails 312, 313, 314. In some embodiments, the movable bucket wheel excavator 301 and the movable stacker 302 may be move by way of continuous tracks 312, 313, 314. As the excavator and stacker progress at substantially the same rate, a gap 303 is maintained between the movable bucket wheel excavator 301 and the movable stacker 302. At a first boundary of gap 303, spent ore material is removed by the moveable bucket wheel extractor 301, and at the second boundary of gap 303, new ore material is deposited by the moveable stacker 302 for leaching.

As shown in FIG. 3 and FIG. 4, leaching pad area module 203 is in the process of being filled with new material, and therefore the leaching pad area module is inactive and is not producing pregnant leaching fluid for processing (though some pregnant fluid may be in the process of being collected for processing). The movable bucket wheel excavator 301 and moveable stacker 302 are moved and positioned according to the associated mine's production schedule. Equipment tracks 312, 313, and 314 allow for this equipment to turn 180 degrees and move to the next section of the leaching area, where leaching pad area modules 211, 212, 213, 214, 215, 216, and 230 are located. In this manner, all of the pads defining the leaching pad area modules 203-206, 210-216, 250, 251, and 230 of leaching area 200 are continuously loaded with ore, irrigated with leaching fluid, and have the spent ore removed.

Again referring to FIG. 3 and FIG. 4, horizontal boreholes 403 and 404 have been drilled at a predetermined depth below ground level 400 and contain muon detectors 104, 105, 106, 107, 108, and 109. In FIG. 3, boreholes 403 and 404 are shown traversing the system of the leaching pad area 200 and the leaching pad area modules 203-206, 210-216, 250, 251, and 230. It should be noted that although the boreholes 403 and 404 are shown traversing the aforementioned system, the number and configuration of the boreholes 403 and 404 is not limited. Other borehole configurations may also advantageous, such as boreholes that traverse a leaching pad area module in a transverse or a slant direction. In some embodiments, the boreholes can be replaced by bored tunnels or trenches excavated prior to the construction of the leaching pad. This can be useful in most implementations, but it is especially cost effective when employed in newly constructed heap leaching operation. This is because in a new deployment, the borehole can be added before being covered with ore, which avoids the need for costly tunneling operations. Borehole 403 and 404 can also be replaced by pipes embedded in a heap such that the pipes are used to collect the pregnant leaching solution that percolates to the bottom of the heap. As shown in FIG. 3 and FIG. 4, the muon detectors 104-109 may move along the boreholes and their position and spacing may be selected according to the measurement needs or operator requirements. For example, in FIG. 3, muon detectors 104 and 105 are positioned relatively close together to provide more coverage in the area between production modules 213 and 214.

One advantage of the configuration shown in FIG. 3 and FIG. 4 is that the muon detectors 104-109 remain in place and may be reused during a cyclical mining operation, such as when spent ore of a leaching pad area module is removed and replaced with new ore to be processed. This configuration thereby enables the same infrastructure of muon detectors, boreholes, and the like to monitor a larger, more productive quantity of ore during operations.

FIG. 4 is a cross sectional side view of the configuration of FIG. 3, showing impermeable liner 410 over ground level 400. The material of the impermeable liner 410 acts as a barrier to contain the process fluid from leaking into the soil. Above impermeable liner 410, a special overliner material 411 is deposited. The overliner material 411 may have a thickness of about 0.5 m to about 1.0 m and is composed of highly permeable materials such that all fluids percolating from leaching pad area modules 211-214 are collected by collection pipes (not shown). The collection pipes are embedded in the overliner. Muon detectors 104, 105, and 108 are positioned in borehole 403 and detect the passage of muon tracks and also the directions which they are intersecting the leaching pad area modules 211, 212, 213, and 214. By reconstructing muon tracks 420-425, it is possible to construct a density map of the heap over time.

The method of drilling boreholes 403 and 404 is not limited, and includes drilling with one or more of a directional drilling tool, a slanted rig (including a coil tubing rig), a tunnel boring machine or a so-called badger or burrowing tool. Boreholes 403 and 404 can be double-ended boreholes with access from both sides and may feature a liner material or casing to protect their inner walls from collapse or deformation as well as to facilitate changing the position of muon detectors 104-109. The muon detectors 104-109 may also be retrieved to allow for maintenance. The muon detectors 104-109 may have wheels or be attached to a track or conveyance system and be pulled or pushed from surface along the length of the borehole. In certain implementations, the wheels may be retractable, spring loaded or able to adjust to different borehole diameters. To facilitate movement of the muon detectors, such wheels may be placed at various points around the azimuth defined by their enclosure. Without loss of generality, wheels may be replaced by rollers to further facilitate conveyance of each muon detector 104-109.

In certain embodiments, the muon detectors are part of a distributed muon detection system. Each individual detector or sensor constitutes a node of such a system, and the distributed muon detection system may be deployed and arranged in order to maximize coverage of the heap according to a survey design methodology. Monte Carlo simulations employed to estimate the count rate, coverage and sensitivity of each muon detector for a given geometry and thickness of the heap are one such survey design methodology capable of optimizing the position of muon detectors while also considering installation and muon detector costs. For instance, in the case of shallow leaching heaps such as those having a thickness of about 3 m, these techniques may be used to determine the preferred depth of boreholes required to optimize coverage of the heap with a few, well-spaced, point-like measurement locations.

Conventional muon detectors are standalone units containing i) a number of sensing elements for determination of track information associated with a muon event; ii) an embedded signal transducer able to digitize event by event the information from the sensing elements, such as a system of photodetectors or a multi-channel photodetector attached to custom signal digitizing electronics; iii) a data communication or telemetry system able to transport the digital information to a remote or local computer host; and iv) a connection to an external power source to provide on-board power required for the read out electronics and the telemetry system.

For the distributed muon detector system disclosed herein, novel configurations may be particularly advantageous. For example, individual nodes according to the disclosure may feature only optical sensing elements (for example, a configuration of scintillator elements) which are connected with optical signal transmission lines, such as one or more flexible fiber optic cables. The fiber optic cables may be routed to one or more processing units, external to the individual nodes, where the signal is subsequently digitized by optical sensors and the event by event information is then processed and transmitted to a computer host. In this way, the individual nodes of the distributed sensor system may not require any electrical power connection. In view of the low signal loss afforded by optical fiber cables, and the relative low cost of optical fiber cables, such a configuration may permit the cost effective connection of multiple passive sensing nodes over distances of up to 100's of meters. When the processing unit is separate from the sensing nodes and positioned outside the observational borehole or trench, a distributed sensor implementation can be very cost effective and particularly convenient for maintenance or troubleshooting.

The nodes in the distributed muon detector system disclosed herein may be independently connected to one or more data communication cables or optical signal transmission lines. The sensing nodes may be passive and feature only the scintillator elements and optical connections, which do not require electrical power. Alternatively, the sensing nodes can be battery operated or connected by a power cable. For instance, the sending nodes may also be connected to a traction cable, including combined multi-function cables that carry signal and/or power and provide a way to move the sensing node. In certain other implementations, data communication to and from a single or multiple sensing nodes may take place via wireless communication. Finally, detector operation, including that of multiple nodes within a distributed muon detector system, may be controlled remotely from a common or shared signal processing unit conveniently located outside of the heap, such as on the surface or in a trench. Data communication to and from the processing unit, including to and from a remote computer host, may utilize either a cellular data network or proprietary communication networks. Similarly, electrical power to the central processing unit or to individual sensor nodes can be provided by a combination of batteries, including batteries replenished by replaceable batteries, solar panel installation, small wind turbines or by gasoline or diesel generators.

A distributed muon detector system in accordance with the disclosure can also be used to survey large structures such as retaining walls built to contain tailing ponds in mining ponds as well as the density of the material in the tailing pond itself. Conventional tailing pond dams and other retaining wall structures are designed with a 2:1 aspect ratio between the base at the foot of the dam and its height. Such a design poses challenges when utilizing the cosmic ray method to determine the distribution of density and water volumes within the structure because the smallest available view angle from the base of the dam could become as large as atan(2/1)~63 degrees from the vertical direction, or even greater when the aspect ratio is even higher. Because the atmospheric muon flux is strongly peaked towards the vertical direction, relatively few muons are available at such large angles which results in reduced statistical accuracy, increased observation time, or both in order to determine density changes.

Figure 5A:
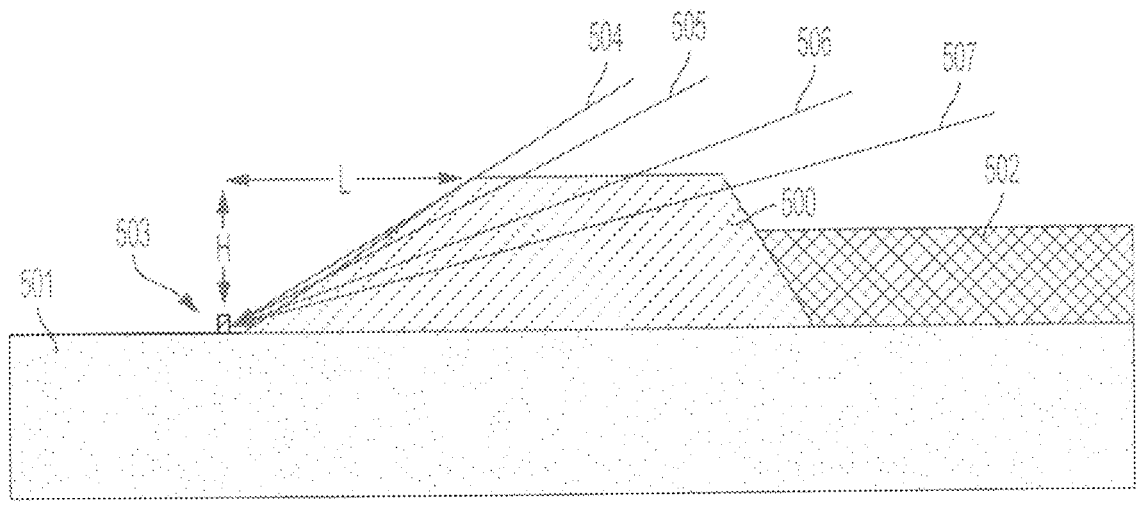
FIG. 5A is a schematic view of at least a portion of a system in accordance with the present disclosure.

Referring to FIG. 5A, a retaining wall 500 is built on hard soil 501 and acts as a dam for a tailing pond 502. When the muon detector 503 is placed at the foot of the dam, the minimum angle at which it can receive useful muon tracks 504-507 is at least $\Theta_{min}$=atan(L/H) from the vertical direction.

Figure 5B:
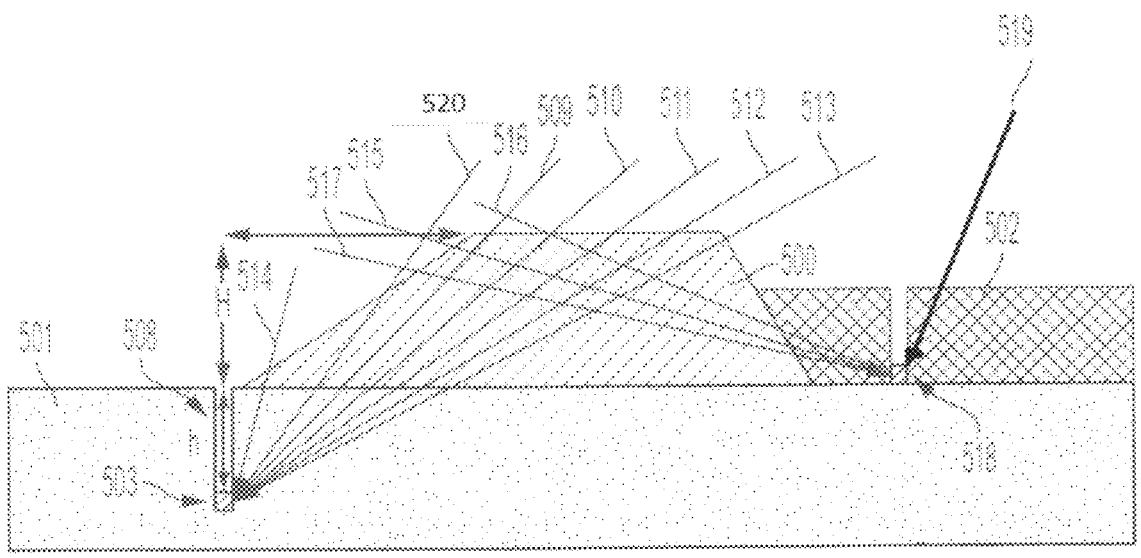
FIG. 5B is a schematic view of at least a portion of a system in accordance with the present disclosure.

In contrast and referring to FIG. 5B, when the muon detector 503 is vertically offset in borehole 508 at the front of the dam, the minimum view angle to the top of the dam become atan(L/(H+h)). Typically, dam heights are in the range of about 50 m to about 150 m, and therefore even a relatively shallow borehole or excavation can improve the situation significantly. In addition, with this implementation, it now becomes possible to analyze the front of the dam as shown by muon tracks 509 to 514 and 520.

In yet other configurations, not exclusive to the above, a muon detector 518 could be placed inside the tailing pond itself, offering access to a different set of muon tracks 515-517 and 519 and view angles with which to further analyze the 3-dimensional distribution of fluids and density inside the dam. This is particularly advantageous for monitoring the densification process at the basis of the pond or soil reclamation as well as determine residual water content in the pond. Furthermore, it is noted that in some situations (not shown), muon tracks may traverse the material of the tailing pond 502 without traversing the dam 500 and subsequently strike muon detector 503 after traversing hard soil 501.

Figure 6:
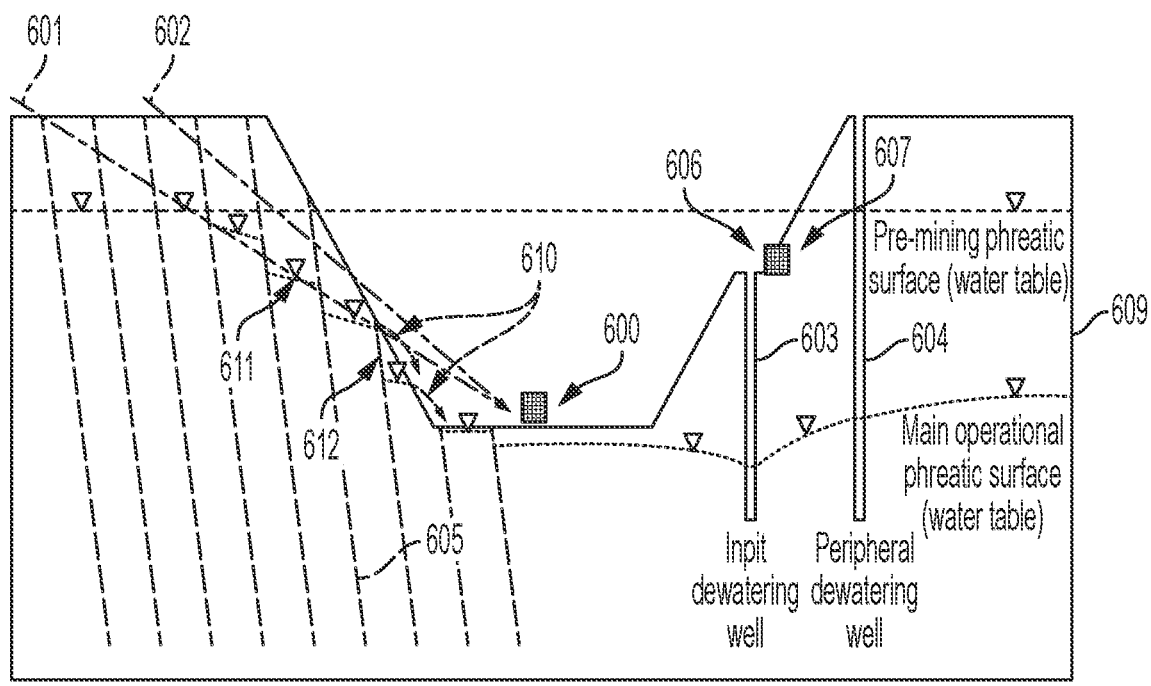
FIG. 6 is a schematic view of at least a portion of a system in accordance with the present disclosure.

Still further, in other implementations and soil stability applications, the muon detector can be placed at the bottom of a pit, such as an open pit where mining operations take place. In this case, the detector may be primarily directed at analyzing the pit wall face as shown in FIG. 6. This configuration can be useful to monitor the stability of the open pit wall.

In FIG. 6, muon detector 600 is placed at the bottom of an open pit and can provide the distribution of fluids behind the pit walls, as indicated by muon tracks 601 and 602. In many cases, pit excavation can reach depths greater than the phreatic water table (609). In such cases, water must be actively managed and pumped in order to continue the operation, for instance with dewatering wells 603 and 604. Nonetheless, the water table tends to rise and return to its original level. Water movements can be facilitated by the possible presence of one or more faults 605 that effectively provide a migration path to water that may result in seepage on the higher portions of the heap. For example, as water moves through the main phreatic surface 611, this results in elevated pore pressure at locations 612, thereby causing water to be discharged from seepage faces 610. When water volume in the walls increases, pore pressure also increases, which leads to a decrease of the shear strength of the rock and an increased risk of slope failure.

In certain embodiments, it may be convenient to place a detector at various points along an access road descending into the pit, e.g. detector 607 at position 606. In yet other embodiments, detectors may also be placed in caves or tunnels specifically prepared to monitor stability of the slope, access a dewatering well or that are specifically made to allow muon detectors to monitor the presence of fluids deep within the pit walls.

For the purpose of building a suitable muon detector, those skilled in the art will recognize that several technologies are available. However, these are not necessarily cost effective or suitable for field use. In one embodiment, a method used to determine the direction of subatomic particles, such as atmospheric muons, may include determining multiple points along the track of the particles. This can be achieved with arrays of elongated strips of scintillator material, including scintillator fibers or sealed channels filled with a liquid scintillator material.

Figure 7:
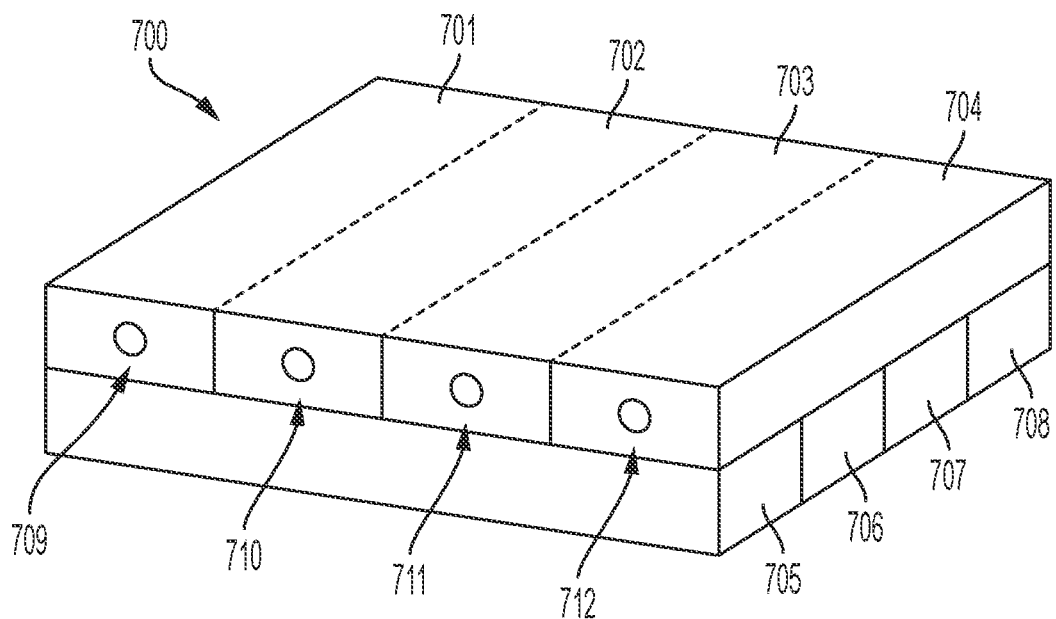
FIG. 7 is a schematic view of a scintillator in accordance with the present disclosure.

Referring to FIG. 7, a scintillator 700 is realized by an arrangement of elongated scintillator elements 701-704 oriented along an X direction, followed by a second plane of elongated scintillator elements (705-708) oriented primarily in an orthogonal Y direction. When a muon traverses such a detector plane, its arrival position can be determined by comparing the data along the X and Y-oriented elongated scintillator elements. A muon detector including at least two such detector planes (i.e. two X- and two Y-planes) will thus be able to determine two points along the cosmic ray track and from there one can calculate the muon's original direction. Typical lengths for each of the scintillator elements are 0.5-2 m in length, 0.5-2 cm in thickness and 1-5 cm in width.

Again referring to FIG. 7, each of the scintillator elements on both planes are directly coupled to multiple optical detectors as shown by 709-712 that are mounted directly to the end of the scintillator elements. In some embodiments, it may be more cost effective or convenient to utilize one common, multi-channel optical detector such as a multi-anode photomultiplier tube or multi-channel solid-state photodetector. In these implementations, elements 709-712 would now simply be optical coupling ports where the scintillation light generated in the scintillator elements is collected onto an optical fiber, such as a plastic or glass optical fiber.

Figure 8:
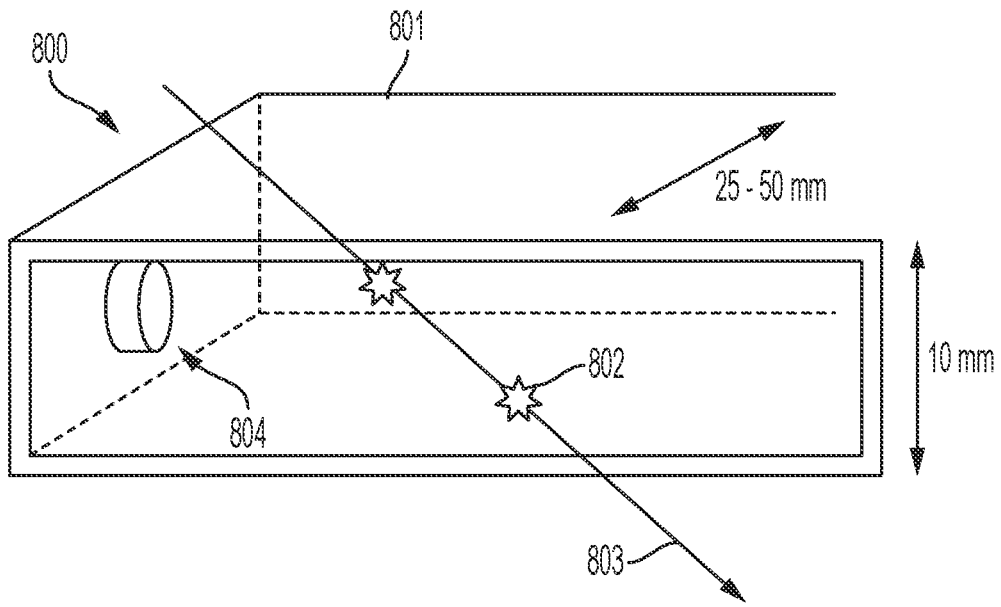
FIG. 8 is a schematic view of a scintillator sensing element in accordance with the present disclosure.

In one embodiment and referring to FIG. 8, the scintillator sensing element 800 is realized by filling an enclosure 801 with a liquid scintillator material 802. In order to maximize the light collection efficiency, while preserving a sealed enclosure, a scintillator element 800 is coupled to a threaded optical fiber collimator 804. Optical fiber collimators have a relatively large diameter lens that can efficiently extract the scintillator light and route it to a conventional optical fiber via a standard connector. Generally, the optical fiber collimator will be separated from the liquid scintillator material by a glass window. In some implementations, the optical fiber collimator assembly may also include a condenser lens that serves to align the light-ray trajectories emerging from the window and facilitate light capture and transmission. As shown in FIG. 8, a muon track 803 generates two scintillation events whose light is collected by the optical collimator 804. Optical fibers are thin and flexible, and thus a preferred choice for routing multiple optical signals onto a single multi-channel optical detector. A threaded collimator insert is particularly advantageous in that it preserves the hermetic seal to the liquid scintillator enclosure and is generally more reliable for field use than any approach relying on a glued optical connection.

An alternate implementation of a muon detector includes a detector plane that includes an array of parallel elongated scintillation sensing elements oriented along one direction with optical read-outs on both ends. The muon arrival position along the direction of each of the elongated scintillator sensor element will be determined by a comparison of the scintillation light collected at both ends, either by comparing different signal amplitudes or arrival times at either end of the sensing element. The muon arrival position in the direction transverse to the elongated scintillator sensing element is determined by the width of each elongated scintillator member.

Figure 9:
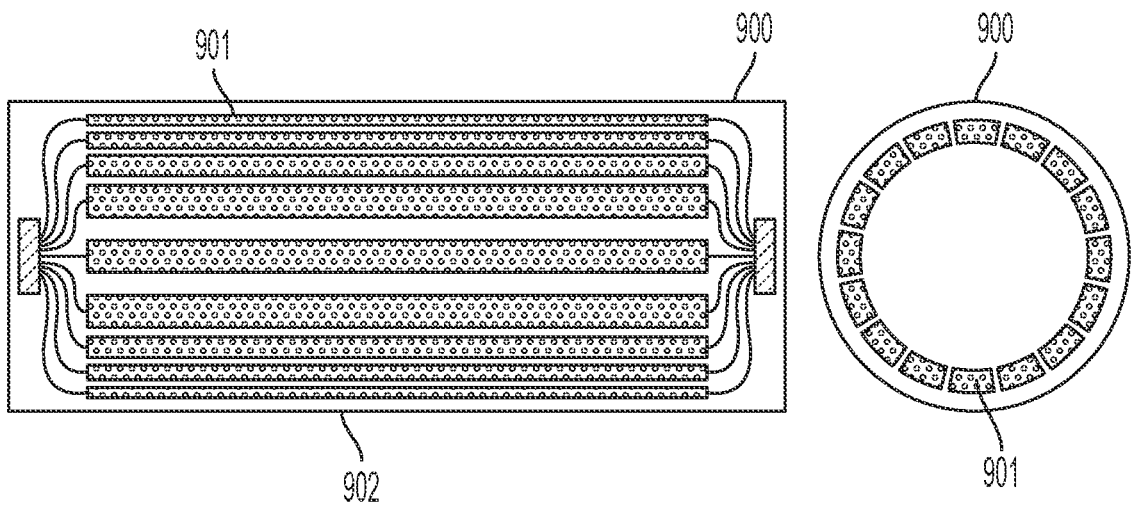
FIG. 9 is a schematic view and a sectional view of an elongated scintillator in accordance with the present disclosure.

In other implementations and referring to FIG. 9, the scintillator 900 includes a plurality of elongated scintillator elements 901 which are arranged within a cylindrical housing 902 in order to fit into a cylindrical enclosure suitable (not shown) for deployment within a borehole. Suitable configurations include those wherein the elongated scintillator sensing elements have a double-sided optical readout and are arranged in an annular pattern and oriented parallel to the housing 902. Additional implementations in which optical fiber collimators are used for the optical readout of each elongated scintillator element are particularly advantageous in a cylindrical detector because the use of thin, flexible optical fibers can achieve further space savings.

In yet other implementations, the cylindrical detector has a hollow core. The hollow core may house the readout and digitizing electronics. In other implementations, the hollow core is at least partially filled with an additional elongated sensor element, for example a non-scintillating detector element such as a Cerenkov light detector. Cerenkov light detectors generate a signal only for ultra-relativistic charged particles travelling at superluminal speeds within its medium, such as with most atmospheric muons travelling through water, and is insensitive to background radiation components such as gamma-rays and neutrons that may otherwise leave an undesired or spurious signal in the scintillator sensing elements. As such, a muon event can be selected by a combination of scintillator and Cerenkov signals which result in a significant background suppression against electronic noise and/or unwanted gamma-ray and neutron signals. Such an embodiment may be particularly useful in cases when the muon detector is installed at shallow depth with the intent of focusing on the so-called hard or high energy component of the atmospheric muon spectrum.

In contrast to scintillator light, which is produced by ionization effects within the scintillator material, the amount of Cerenkov light produced by an ultra-relativistic muon is proportional to the muon energy. Accordingly, the detected amount of Cerenkov light provides additional information about the energy of the incoming muon. In addition, for a given muon energy, Cerenkov light is emitted at a fixed angle relative to the muon trajectory. Using such information, the angle at which Cerenkov light is emitted can be reconstructed, which may allow the determination of further information related to the muon track. This is typically done by reconstructing a ring of light emission with a segmented, multi-channel photo-detector. Such a ring-imaging detector can also be used in an underground muon detector to, for example, collect the Cerenkov signal at multiple points around the Cerenkov radiating element.

Water is a preferred Cerenkov radiator for atmospheric muons. Indeed, in all of the above-listed detector implementations, water-based Cerenkov radiators may be used in place of the liquid or plastic scintillation sensing elements.

Figure 10A:
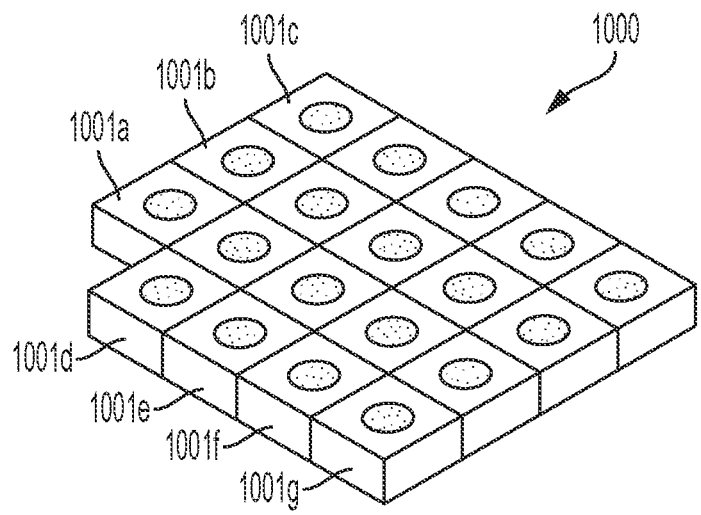
FIG. 10A is a schematic view of a muon detector in accordance with the present disclosure.
Figure 10B:
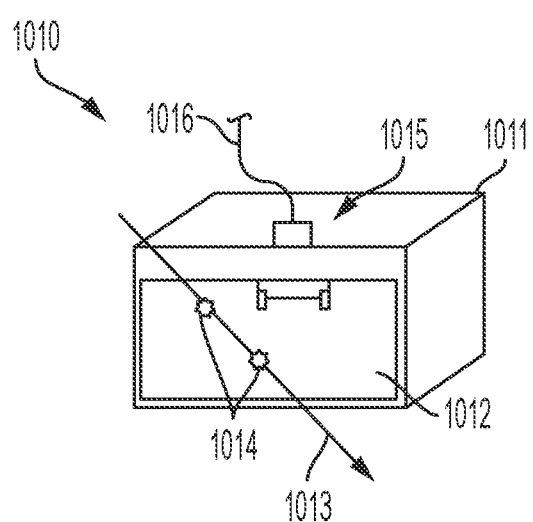
FIG. 10B is a schematic view of a muon detector in accordance with the present disclosure.

In still other embodiments and referring to FIGS. 10A and 10B, each detector plane in the muon detector may be realized using an arrangement of a primarily cubical scintillator or Cerenkov elements used to form a pixel detector. FIG. 10A shows one embodiment of a pixel detector 1000 which includes an array of pixels 1001a, 1001b, 1001c, 1001d, 1001e, 1001f, 1001g (note that the interior pixels of the array of pixels are not labeled). The array of pixels can be viewed through a readout window (not shown). In another variation shown in FIG. 10B, the channels are filled with a liquid scintillator In FIG. 10B, liquid scintillator 1010 includes at least one chamber 1011 which is filled with scintillating liquid 1012. When one or more atmospheric muons 1013 impinge the chamber 1011 and scintillating liquid 1012, the scintillating liquid 1012 emits light 1014. The emitted light 1014 is collected by optical collimation system 1015 that is coupled with one or more optical fibers 1016. The optical fibers 1016 transmit the light to one or more photodetectors (not shown) which produce an electrical signal that thereby indicates the passage of atmospheric muons. Two layers of pixel detectors may be used in place of crossed layers of elongated scintillator sensor elements with either single- or double-sided optical readout. Typical scintillator members in a pixel detector may have a width of about 5 mm to about 50 mm, a depth of about 5 mm to about 50 mm, and a height of about 5 mm to about 15 mm.

Gaseous charged particle detectors, including multi-wire chambers, gaseous electron multipliers (GEMs), time projection chambers, or arrays of small diameter proportional or Geiger tubes may also be suitable as an alternative to scintillation detectors for the purpose of detecting and determining the track direction of atmospheric and underground muons.

After a muon-tracking detector is placed beneath a mining heap, a stockpile, a dam wall, including a retaining pond wall, or an open pit wall, the directional measurement of the flux of atmospheric or underground muons can provide a map of the bulk density distribution of the volume under consideration, including areas of excess density due to water accumulation over time. Such information can be used to provide advanced diagnostic information regarding the risk of slope failures or to optimize metal extraction via heap leaching or water recovery processes.

While muon detectors primarily measure bulk density, such information may be combined with a variety of other methods to arrive at a better determination of slope stability parameters, economic value and leaching or dewatering processing time. Such additional data may come from gravity, EM, resistivity or seismic surveys, borehole measurements (e.g. temperature, pressure density, resistivity, nuclear spectroscopy, etc.) and sampling data (cores, fluids collection, etc.).

Slope failure is ultimately related to pore pressure. Pore pressure increases as a function of water volumes, which can be identified by an analysis of excess density distribution. A deep-reading, geo-spatial monitor such as the one disclosed herein can provide unique information about the presence of risk areas and be used to inform an early warning system to alert the operator of possible slope failures. The information collected in this way can also be used to trace underground water movement to its source and thus design effective dewatering techniques and interventions. The information provided by the muon density measurement can also be used to determine whether other dewatering techniques should be used including the location and depth of dewatering wells. In the case of a leaching heap, the operator may adjust the irrigation schedule, including flow, volume and location of irrigation lines, accordingly in order to minimize the risk of slope failures or to maximize metal recovery.

The slope stability analysis described above can be used to determine safe operating zones for the access of mining equipment and heavy machinery. When fluid volumes are too high, the risk of such equipment at least partially sinking into the unconsolidated material increases, which can result in a significant loss of access and productive time. This problem can occur in leaching pads, but may also occur on exposed mining access roads, which are important in many mining operations, including open pit mining.

In the case of a leaching heap, the deep-reading, geospatial information regarding the volume and location of leaching agent at different points across the heap provided by the muon detectors can also be used to better estimate the Net Present Value (NPV) of the asset.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 devices refers to groups having 1, 2, or 3 devices. Similarly, a group having 1-5 devices refers to groups having 1, 2, 3, 4, or 5 devices, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A method of monitoring slope stability by determining a density of at least a portion of a heap by measuring an incidence of atmospheric muons, the method comprising:
   associating a muon detector with the heap by placing the muon detector within an overliner material, measuring an incidence of atmospheric muons on the muon detector, and determining the density of a portion of the heap by comparing the incidence of atmospheric muons detected by the muon detector to a muon attenuation of a material in the heap and a muon flux at an earth surface.

2. The method of claim 1, wherein comparing includes one or more of:

comparing an initial muon attenuation for an initial density from an initial sample of the materials of the heap with the muon attenuation in the heap, comparing a prior time interval muon attenuation in the heap as measured during a prior time interval with the muon attenuation in the heap, comparing a fluid muon attenuation of process fluids with the measured incidence of atmospheric muons on the muon detector, or comparing the muon attenuation in the heap to a muon flux at the earth surface including a surface flux measured by a secondary detector.

3. The method of claim 2, wherein the initial sample of the materials of the heap is one or more of a dry ore sample, a pre-wetted ore sample, or agglomerated ore.

4. The method of claim 2, wherein the initial sample of materials of the heap comprises materials from two or more different locations in the heap.

5. The method of claim 2, wherein the measured incidence of atmospheric muons is measured by detecting at least two muon tracks that are oriented in different directions.

6. The method of claim 1, further comprising moving at least one muon detector.

7. The method of claim 1, wherein the heap includes two or more leaching pad area modules.

8. The method of claim 1, wherein the heap is a dam.

9. The method of claim 8, wherein associating the muon detector includes placing the muon detector that is horizontally offset from the toe of the dam or placing the muon detector that is horizontally offset inside the dam and beneath materials held by the dam.

10. The method of claim 1, further comprising determining a fluid content of a portion of the heap by measuring a change in an apparent bulk density of the unconsolidated material in the portion of the heap between an initial sample value and a current value.

11. A system for monitoring slope stability by determining a density of a portion of a heap by measuring an incidence of atmospheric muons, the system comprising:

a muon detector associated with the heap by being located within an overliner material, wherein the system measures an incidence of atmospheric muons on the muon detector, and wherein the system determines the density of the portion of the heap by comparing the incidence of atmospheric muons detected by the muon detector to an initial muon attenuation of the materials in the heap and an initial muon flux at an earth surface.

12. The system of claim 11, wherein the heap includes two or more leaching pad area modules.

13. The system of claim 11, wherein the heap is a dam.

14. The system of claim 13, wherein the muon detector is placed horizontally offset from the heap outside of the dam or is placed inside the dam and beneath the materials being held by the dam.

15. The system of claim 11, wherein the system further determines a fluid content of a portion of the heap by measuring, a change in an apparent bulk density of unconsolidated material in the portion of the heap between an initial sample value and a current value.

* * * * *